United States Patent [19]

Pommer et al.

[11] 4,104,399

[45] Aug. 1, 1978

[54] TRIAZOLE DERIVATIVES

[75] Inventors: Ernst-Heinrich Pommer, Limburgerhof; Klaus Gutsche, Rellingen; York Hartleben, Heist, all of Fed. Rep. of Germany

[73] Assignee: BASF Aktiengesellschaft, Ludwigshafen, Fed. Rep. of Germany

[21] Appl. No.: 839,761

[22] Filed: Oct. 6, 1977

[30] Foreign Application Priority Data

Nov. 17, 1976 [DE] Fed. Rep. of Germany ....... 2652313

[51] Int. Cl.$^2$ .......................................... C07D 249/08
[52] U.S. Cl. .................................. 424/269; 542/468; 542/454; 542/462
[58] Field of Search ................ 424/269; 542/468, 454, 542/462

[56] References Cited

U.S. PATENT DOCUMENTS

| | | | |
|---|---|---|---|
| 3,682,950 | 8/1972 | Buchel et al. | 424/269 |
| 3,972,892 | 8/1976 | Buchel et al. | 424/269 |
| 3,974,174 | 8/1976 | Buchel et al. | 424/269 |

*Primary Examiner*—Arthur P. Demers
*Attorney, Agent, or Firm*—Keil, Thompson & Shurtleff

[57] ABSTRACT

New and valuable triazole derivatives having a good fungicidal action, fungicides containing these compounds as active ingredients, and methods of combatting fungi with these compounds.

1 Claim, No Drawings

TRIAZOLE DERIVATIVES

The present invention relates to new and valuable triazole derivatives and salts thereof, processes for their manufacture, and their use as fungicides.

It is disclosed in German Laid-Open Application DOS 2,063,857 that 1-[2-(2,4-dichlorophenyl)-2-(2-propenyloxy)-ethyl]-1H-imidazole has a fungicidal action. Its action is insufficient, particularly on mildews and rusts. For this reason, it is hardly suitable as a crop protection agent for combatting fungi.

We have now found that the new triazole derivatives of the formula

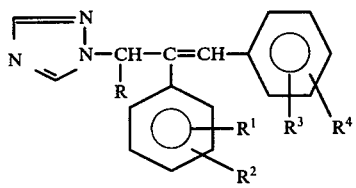

where R denotes hydrogen, lower alkyl (methyl) or phenyl, $R^1$ denotes hydrogen or halogen (F, Cl, Br), $R^2$ denotes hydrogen or halogen (F, Cl, Br), $R_3$ denotes hydrogen, halogen (F, Cl, Br) or methoxy, and $R^4$ denotes hydrogen, halogen (F, Cl, Br), methoxy or methyl, and salts thereof, have a good action on injurious fungi, especially those from the Ascomycetes and Basidiomycetes classes.

We have further found that triazole derivatives of the formula I and their salts are obtained by reacting a ketone of the formula

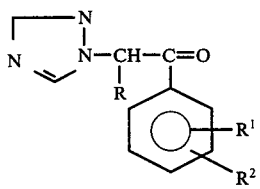

where R, $R^1$ and $R^2$ have the above meanings, in the presence of an alkaline compound with a phosphorus derivative of the formula

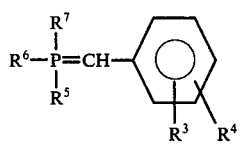

where $R^3$ and $R^4$ have the above meanings and $R^5$, $R^6$ and $R^7$ are identical or different and each denotes phenyl, p-carboxyphenyl, p-dimethylaminophenyl, dimethylamino, piperidine, morpholine, alkyl of 1 to 3 carbon atoms, or cyclohexyl. This manufacturing method is preferred.

The triazole derivatives of the formula I are also obtained by reacting a ketone of the formula II in the presence of an alkaline compound with a phosphorus derivative of the formula

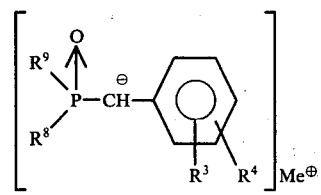

where $R^3$ and $R^4$ have the above meanings and $R^8$ and $R^9$ are identical or different and each denotes phenyl or, preferably, alkoxy of from 1 to 3 carbon atoms and Me denotes an alkali metal. The new compounds may be in the trans or cis isomer form, or a mixture thereof.

Similar reactions are disclosed in the literature, e.g., Organic Reactions, 14, chapter 3, 270–490, and Houben-Weyl, Methoden der organischen Chemie, 5/1b, 383–418.

The ketones of the formula II are disclosed for instance in German Laid-Open Application DOS 2,431,407. The phosphorus derivatives of the formula III are disclosed for instance in Organic Reactions, 14, 405. The phosphorus derivatives of the formula IV are disclosed for instance in Houben-Weyl, 5/1b, 397. The reaction described above of a ketone of the formula II with a phosphorus derivative of the formula III may be carried out without a diluent, which may be of advantage for achieving higher reaction temperatures. However, the reactions described above may also be carried out in the presence of diluents. Examples of such diluents are various ethers such as diethyl ether, tetrahydrofuran or ethylene glycol dimethyl ether; alcohols; hydrocarbons such as hexane or benzene; dimethyl sulfoxide, dimethylformamide or liquid ammonia. Depending on the conditions selected, the compounds according to the invention are obtained as a cis-trans isomer mixture, which, if desired, may be split into its isomers by conventional methods, e.g., fractional crystallization, or are obtained direct as cis or trans isomers.

The reactions are carried out in the presence of alkaline compounds such as lithium phenyl, lithium butyl, alkali metal alcoholates, sodium amide, sodium hydride or sodium dimethylsulfoxilate.

The reactions are carried out at temperatures of from 0° to 100° C, preferably from 20° to 50° C. Treatment of the compounds obtained in accordance with these processes with acids gives their salts.

The new triazole derivatives and their salts have a much wider spectrum of fungicidal action and are better tolerated by crop plants than the prior art compound 1-[2-(2,4-dichlorophenyl)-2-(2-propenyloxy)-ethyl]-1H-imidazole.

The new active ingredients may also be used in the form of their salts, e.g., hydrochlorides, hydrobromides, sulfates, oxalates, dodecylbenzene sulfonates or nitrates.

The fungicidal agents according to the invention are of considerable interest for combatting fungus diseases, e.g., *Ustilato scitaminea, Hemileia vastatrix, Uromyces fabae* or *appendiculatus, Puccinia* species, *Erysiphe graminis, Botrytis cinerea* in vines and strawberries, *Uncinula necator, Sphaerotheca fuliginea, Erysiphe cichoracearum* and *Podosphaera leucotricha,* in various crop plants, especially wheat, rye, barley, oats, rice, Indian corn, apples, cucumbers, beans, coffee, sugar cane, vines, strawberries, and ornamentals in horticulture.

The active ingredients according to the invention have a systemic action, which is of particular interest in connection with the fight against internal plant diseases such as rust and mildew in cereals.

The agents according to the invention may simultaneously suppress the growth of two or more of the abovementioned fungi, and are excellently tolerated by crop plants. The application rates for combatting phytophathogenic fungi are from 0.05 to 2 kg of active ingredient per hectare.

The preparation of the new compounds is illustrated by the following examples.

EXAMPLE 1

8 g of 2,4-dichlorobenzyltriphenylphosphonium chloride and 4.5 g of 2,4-dichloro-ω-(1,2,4-triazolyl-1)-acetophenone are dissolved in 250 ml of methanol. A solution of 0.5 g of sodium in 20 ml of methanol is then added and the whole is refluxed for 3 hours. The solvent is distilled off, the residue is stirred with water, and the semisolid product is recrystallized from benzene.

There is obtained 4.6 g (66% of theory) of cis-1,2-di-(2,4-dichlorophenyl)-3-(1,2,4-triazolyl-1)-propene-1 having a melting point of 116° to 120° C (compound no. 9 in the table below).

EXAMPLE 2

5 g of cis-1,2-di-(2,4-dichlorophenyl)-3-(1,2,4-triazolyl-1)-propene-1 is dissolved in 100 ml of isopropyl ether. 10 ml of 10 wt% ethanolic hydrochloric acid is then added.

There is obtained a precipitation of 4.8 g of the hydrochloride having a melting point of 188° to 190° C (compound no. 10 in the table below).

EXAMPLE 3

5.4 g of 2,4-dichloro-ω-(1,2,4-triazolyl-1)-acetophenone and 14.4 g of 2,4-dichlorobenzyltriphenylphosphonium chloride are suspended in 250 ml of benzene. After the addition of 3.5 g of potassium tert-butylate the mixture is refluxed for 12 hours. The benzene is then distilled off, the residue is dissolved in 100 ml of ethanol, and concentrated nitric acid is added until the solution has an acid reaction. By diluting the solution with water, an oily product is obtained which, after recrystallization from isopropanol, gives 5 g (52% of theory) of trans-1,2-di-(2,4-dichlorophenyl)-3-(1,2,4-triazolyl-1)-propene-1-nitrate having a melting point of 135° to 140° C (compound no. 6 in the table below).

EXAMPLE 4

5 g of the nitrate obtained in Example 3 is dissolved in 50 ml of ethanol. There is then added 50 ml of an approx. 10% strength aqueous ammonia solution. 3.5 g of trans-1,2-di-(2,4-dichlorophenyl)-3-(1,2,4-triazolyl-1)-propene-1 crystallizes out; melting point: 118° to 119° C (compound no. 11 in the table below).

EXAMPLE 5

22 g of 4-chloro-ω-(1,2,4-triazolyl-1)-acetophenone, 30 g of diethyl 2,4-dichlorobenzylphosphonate and 20 g of potassium tertbutylate are refluxed for 10 hours in 500 ml of benzene. After the solution has been cooled it is stirred into 2 liters of water and the benzene phase is separated and dried with solid $K_2CO_3$. While cooling, 100% nitric acid is added to the benzene solution until it has an acid reaction; the precipitate which is obtained is recrystallized from isopropanol.

There is obtained 29 g (68% of theory) of trans-1-(2,4-dichlorophenyl)-2-(4-chlorophenyl)-3-(1,2,4-triazolyl-1)-propene-1-nitrate having a melting point of 174° to 177° C (compound no. 8 in the table below).

The following compounds were prepared analogously:

| No. | R | isomer | $R^1$ | $R^2$ | $R^3$ | $R^4$ | salt | m.p. (° C) |
|---|---|---|---|---|---|---|---|---|
| 1 | H | trans | H | H | H | H | $HNO_3$ | 132–134 |
| 2 | H | trans | H | H | H | 4-Cl | $HNO_3$ | 150–152 |
| 3 | H | cis/trans | H | 4-Br | H | 4-Cl | $HNO_3$ | 152–153 |
| 4 | H | cis/trans | H | 4-Cl | H | 4-Cl | $HNO_3$ | 147–149 |
| 5 | H | trans | H | 4-Cl | 2-Cl | 4-Cl | $HNO_3$ | 150–153 |
| 6 | H | trans | 2-Cl | 4-Cl | 2-Cl | 4-Cl | $HNO_3$ | 135–140 |
| 7 | H | cis/trans | 2-Cl | 4-Cl | H | 4-Br | $HNO_3$ | 164–165 |
| 8 | H | trans | 2-Cl | 4-Cl | H | 4-Cl | $HNO_3$ | 174–177 |
| 9 | H | cis | 2-Cl | 4-Cl | 2-Cl | 4-Cl | — | 116–120 |
| 10 | H | cis | 2-Cl | 4-Cl | 2-Cl | 4-Cl | $HNO_3$ | 188–190 |
| 11 | H | trans | 2-Cl | 4-Cl | 2-Cl | 4-Cl | — | 118–119 |
| 12 | H | trans | H | H | H | 4-Br | — | 143–144 |
| 13 | H | trans | H | H | 2-Cl | 5-Cl | $HNO_3$ | 150–152 |
| 14 | H | trans | H | H | 2-OCH$_3$ | H | $HNO_3$ | 152–154 |
| 15 | H | trans | H | H | H | 4-OCH$_3$ | $HNO_3$ | 110–112 |
| 16 | H | trans | 3-Cl | 4-Cl | H | 4-Cl | — | 163–164 |
| 17 | H | cis/trans | 3-Cl | 4-Cl | H | 4-CH$_3$ | $NHO_3$ | 150–152 |
| 18 | H | cis/trans | H | 4-Cl | H | 4-CH$_3$ | $HNO_3$ | 138–140 |
| 19 | H | cis/trans | 2-Cl | 4-Cl | H | 4-CH$_3$ | $HNO_3$ | 147–148 |
| 20 | $C_6H_5$ | trans | 3-Cl | 4-Cl | H | H | $HNO_3$ | 98–100 |
| 21 | $CH_3$ | cis/trans | H | H | H | 4-Br | $HNO_3$ | 151–153 |
| 22 | $CH_3$ | cis/trans | 2-Cl | 4-Cl | H | 4-Br | $HNO_3$ | 153–155 |
| 23 | $CH_3$ | cis/trans | 3-Cl | 4-Cl | H | 4-Br | $HNO_3$ | 156–157 |
| 24 | $CH_3$ | cis/trans | H | 4-Cl | H | 4-Br | $HNO_3$ | 145–147 |
| 25 | $CH_3$ | trans | 3-Cl | 4-Cl | H | 4-CH$_3$ | $HNO_3$ | 158–160 |
| 26 | $CH_3$ | trans | H | 4-Cl | H | 4-CH$_3$ | $HNO_3$ | 156–158 |
| 27 | $CH_3$ | trans | 2-Cl | 4-Cl | H | 4-CH$_3$ | $HNO_3$ | 149–151 |

The active ingredients according to the invention may be converted into the usual formulations such as solutions, emulsions, suspensions, powders, pastes and granules. The formulations are prepared in known manner, e.g., by mixing the active ingredient with solvents and/or carriers, if desired with emulsifiers and dispersants; when water is used as diluent other organic solvents may also be employed as auxiliary solvents. The most suitable auxiliaries are solvents, such as aromatics (e.g., xylene, benzene), chlorinated aromatics (e.g., chlorobenzenes), paraffins (e.g., petroleum fractions), alcohols (e.g., methanol, butanol), amines (e.g., ethanolamine, dimethylformamide) and water; carriers, such as natural rock flours (e.g., kaolins, clays, talc, chalk) and synthetic rock flours (e.g., highly disperse silicic acid, silicates); emulsifying agents, such as non-ionogenic and anionic emulsifiers (e.g., polyoxyethylene fatty alcohol ethers, alkyl sulfonates and aryl sulfonates); and dispersants such as lignin, sulfite waste liquors and methyl cellulose.

The formulations generally contain from 0.1 to 95, preferably from 0.5 to 90, wt% of active ingredient. The formulations, or the ready-for-use preparations made therefrom, such as solutions, emulsions, suspensions, powders, pastes and granules, are applied in known manner, e.g., by spraying, atomizing, dusting, broadcasting, watering, or treating seed with them.

The agents according to the invention may also be applied in admixture with other active ingredients, e.g., herbicides, insecticides, growth regulators and fungicides, and also with fertilizers. Examples of fungicides which may be combined with the compounds of the invention are dithiocarbamates and derivatives thereof, e.g.,
ferric dimethyldithiocarbamate
zinc dimethyldithiocarbamate
manganese ethylenebisdithiocarbamate
zinc ethylenebisdithiocarbamate
tetramethylthiuram disulfide
manganese-zinc ethylenediamine-bisdithiocarbamate
zinc-(N,N'-propylene-bisdithiocarbamate)
ammonia complex of zinc-(N,N'-ethylene-bisdithiocarbamate)
and
N,N'-polyethylene-bis-(thiocarbamoyl)-disulfide
ammonia complex of zinc-(N,N'-propylene-bisdithiocarbamate)
and
N,N'-polypropylene-bis-(thiocarbamoyl)-disulfide
nitrophenol derivatives, such as
dinitro-(1-methylheptyl)-phenylcrotonate
2-sec-butyl-4,6-dinitrophenyl-3,5-dimethylacrylate
2-sec-butyl-4,6-dinitrophenylisopropylcarbonate
heterocyclic structures, such as
N-trichloromethylthiotetrahydrophthalimide
N-trichloromethylthiophthalimide
2-heptadecyl-2-imidazoline acetate
2,4-dichloro-6-(o-chloroanilino)-s-triazine
0,0-diethylphthalimidophosphonothioate
5-amino-1-[bis-(dimethylamino)-phosphynyl]-3-phenyl-1,2,4-triazole
5-ethoxy-3-trichloromethyl-1,2,4-thiadiazole
2,3-dicyano-1,4-dithiaanthraquinone
2-thio-1,3-dithio-[4,5-b]-quinoxaline
methyl 1-(butylcarbamoyl)-2-benzimidazole carbamate
2-methoxycarbonylaminobenzimidazole
2-thiocyanomethylthiobenzothiazole
4-(2-chlorophenylhydrazono)-3-methyl-5-isooxazolone pyridine-2-thiol-1-oxide
8-hydroxyquinoline and its copper salt
2,3-dihydro-5-carboxanilido-6-methyl-1,4-oxathiin-4,4-dioxide
2,3-dihydro-5-carboxanilido-6-methyl-1,4-oxathiin
2-[furyl-(2)]-benzimidazole
piperazine-1,4-diyl-bis[1-(2,2,2-trichloroethyl)-formamide]
2-[thiazolyl-(4)]-benzimidazole
5-butyl-2-dimethylamino-4-hydroxy-6-methylpyrimidine
bis-(p-chlorophenyl)-3-pyridinemethanol
1,2-bis-(3-ethoxycarbonyl-2-thioureido)-benzene
1,2-bis-(3-methoxycarbonyl)-2-thioureido)-benzene
and various fungicides, such as dodecylguanidine acetate 3-[2-(3,5-dimethyl-2-oxycyclohexyl)-2-hydroxyethyl]-glutarimide hexachlorobenzene
N-dichlorofluoromethylthio-N',N'-dimethyl-N-phenylsulfuric acid diamide
2,6-dimethyl-N-tridecylmorpholine and its salts
2,6-dimethyl-N-cyclododecylmorpholine and its salts
2,5-dimethylfuran-3-carboxylic acid anilide
2,5-dimethylfuran-3-carboxylic acid cyclohexyl amide
2-methylbenzoic acid anilide
2-iodobenzoic acid anilide
1-(3,4-dichloroanilino)-1-formylamino-2,2,2-trichloroethane
2,3-dichloro-1,4-naphthoquinone
1,4-dichloro-2,5-dimethoxybenzene
p-dimethylaminobenzenediazosodium sulfonate
2-chloro-1-nitropropane
polychloronitrobenzenes, such as pentachloronitrobenzene,
methyl isocyanate, fungicidal antibiotics such as
griseofulvin and kasugamycin, tetrafluorodichloroacetone,
1-phenylthio semicarbazide, Bordeaux mixture, nickel-containing compounds and sulfur.

In the fight against mildew and rust diseases in cereals, synergism was achieved when using the new compounds, either as bases or salts, in admixture with N-tridecyl-2,6-dimethylmorpholine or its salts. The increase in action is particularly evident in the ratio range of from 1:2 to 1:4 parts bhy weight.

The following examples illustrate the fungicidal action of the new active ingredients.

EXAMPLE 6

Barley mildew

Leaves of barley seedlings grown in pots are sprayed with aqueous emulsions consisting of 80% of active ingredient and 20% of emulsifier and dusted, after the sprayed-on layer has dried, with spores of barley mildew (Erysiphe graminis var. hordei). The plants are then placed in a greenhouse at from 20° to 22° C and 75 to 80% relative humidity. The extent of fungus spread is determined after 10 days.

| Active ingredient | Leaf attack after spraying with liquors containing active ingredient in amounts of | |
|---|---|---|
| | 0.025% | 0.012% |
| Control (untreated) | 5 | |
| 1 | 0 | 2 |
| 2 | 0 | 1 |
| 3 | 1 | 1 |
| 4 | 0 | 1 |
| 5 | 0 | 0 |
| 6 | 0 | 0 |
| 7 | 0 | 0 |
| 8 | 0 | 2 |
| (comparative agent) | 1 | 3 |

[structure: N-containing ring—CH$_2$—CH(—O—CH$_2$—CH=CH$_2$)—C$_6$H$_3$Cl$_2$]

0 = no damage, graduated down to 5 = surface of leaves completely covered by fungus

EXAMPLE 7

Wheat mildew and leaf rust

Leaves of wheat seedlings of the "Jubilar" variety grown in pots are sprayed with aqueous emulsions consisting of 80% of active ingredient and 20% emulsifier and dusted, after the sprayedon layer has dried, with spores of wheat mildew (*Erysiphe graminis var. tritici*). In the experiments with wheat leaf rust (*Puccinia recondita*), the wheat seedlings are artificially infected with rust spores 24 hours before spraying, and placed in a steamsaturated chamber kept at from 20° to 25° C. The plants are then placed in a greenhouse at from 20° to 22° C and 75 to 80% relative humidity. The extent of fungus spread is determined after 10 days.

| Active ingredient | Attack after spraying with liquors containing active ingredient in amounts of | | | |
|---|---|---|---|---|
| | 0.025% (mildew) | 0.012% (mildew) | 0.05% (leaf rust) | 0.025% (leaf rust) |
| Control (untreated) | 5 | | 5 | |
| 1 | — | — | 2 | 3 |
| 2 | 1 | 1 | 0 | 2 |
| 3 | 1 | 1 | 0 | 1 |
| 4 | 1 | 1 | 0 | 0 |
| 5 | 0 | 2 | 0 | 0 |
| 6 | 0 | 0 | 0 | 2 |
| 7 | 1 | 1 | 0 | 2 |
| 8 | 1 | 3 | 0 | 1 |
| (comparative agent) | 3 | 4 | 3 | 5 |

0 = no damage, graduated down to 5 = surface of leaves completely covered by fungus

EXAMPLE 8

Cucumber mildew

Leaves of cucumber seedlings grown in pots are sprayed with aqueous emulsions consisting of 80% of active ingredient and 20% of emulsifier and dusted, after the sprayed-on layer has dried, with spores of cucumber mildew (Erysiphe cichoriacearum). The plants are then placed in a greenhouse at from 20° to 22° C and 75 to 80% relative humidity. The extent of fungus spread is determined after 10 days.

| Active ingredient | Leaf attack after spraying with liquor containing active ingredient in an amount of 0.05% |
|---|---|
| 2 | 0 |
| 3 | 0 |
| 4 | 0 |
| 6 | 0 |
| 7 | 0 |
| 8 | 0 |
| (comparative agent) | 2 |

EXAMPLE 9

90 parts by weight of compound 9 is mixed with 10 parts by weight of N-methyl-α-pyrrolidone. A mixture is obtained which is suitable for application in the form of very fine drops.

EXAMPLE 10

20 parts by weight of compound 2 is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 11

20 parts by weight of compound 3 is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 12

20 parts by weight of compound 4 is dissolved in a mixture consisting of 25 parts by weight of cyclohexanol, 65 parts by weight of a mineral oil fraction having a boiling point between 210° and 280° C, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 13

20 parts by weight of compound 5 is well mixed with 3 parts by weight of the sodium salt of diisobutylnaphthalene-α-sulfonic acid, 17 parts by weight of the sodium salt of a ligninsulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 14

3 parts by weight of compound 6 is intimately mixed with 97 parts by weight of particulate kaolin. A dust is obtained containing 3% by weight of the active ingredient.

EXAMPLE 15

30 parts by weight of compound 7 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 16

40 parts by weight of compound 9 is intimately mixed with 10 parts of the sodium salt of a phenolsulfonic acid-urea-formaldehyde condensate, 2 parts of silica gel and 48 parts of water to give a stable aqueous dispersion. Dilution in 100,000 parts by weight of water gives an aqueous dispersion containing 0.04 wt% of active ingredient.

EXAMPLE 17

20 parts of compound 8 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

We claim:

1. Triazole derivatives of the formula

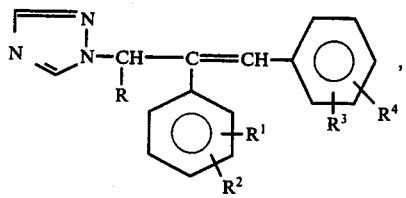

where R denotes hydrogen, lower alkyl or phenyl, $R^1$ denotes hydrogen or halogen, $R^2$ denotes hydrogen or halogen, $R^3$ denotes hydrogen, halogen or methoxy, and $R^4$ denotes hydrogen, halogen, methoxy or methyl, and salts thereof.

2. A process for combatting fungi, wherein plants or their seed are treated with a triazole derivative of the formula

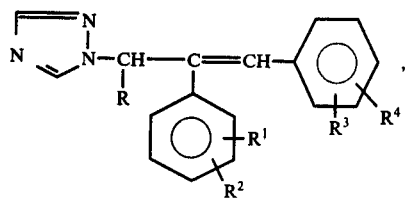

where R denotes hydrogen, lower alkyl or phenyl, $R^1$ denotes hydrogen or halogen, $R^2$ denotes hydrogen or halogen, $R^3$ denotes hydrogen, halogen or methoxy, and $R^4$ denotes hydrogen, halogen, methoxy or methyl, or a salt thereof.

3. The compound of the formula

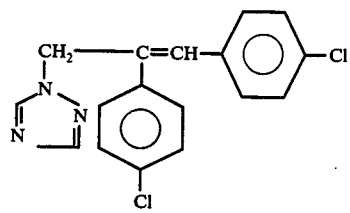

4. The compound of the formula

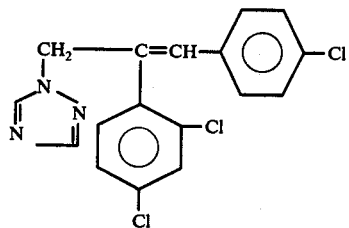

5. The compound of the formula

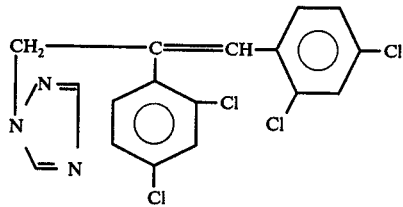

* * * * *